United States Patent
Gaisser et al.

(10) Patent No.: US 9,922,534 B2
(45) Date of Patent: *Mar. 20, 2018

(54) AUTOMATIC HYGIENE COMPLIANCE ASSISTANCE

(71) Applicant: Versus Technology, Inc., Traverse City, MI (US)

(72) Inventors: Gary T. Gaisser, Kingsley, MI (US); Henry J. Tenarvitz, Suttons Bay, MI (US)

(73) Assignee: VERSUS TECHNOLOGY, INC., Traverse City, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/295,544

(22) Filed: Oct. 17, 2016

(65) Prior Publication Data
US 2017/0032657 A1    Feb. 2, 2017

Related U.S. Application Data

(63) Continuation of application No. 14/335,015, filed on Jul. 18, 2014, now Pat. No. 9,497,428.
(Continued)

(51) Int. Cl.
*G08B 23/00*     (2006.01)
*G08B 21/24*     (2006.01)
(Continued)

(52) U.S. Cl.
CPC .......... *G08B 21/245* (2013.01); *A47K 5/1217* (2013.01); *G06F 19/327* (2013.01);
(Continued)

(58) Field of Classification Search
CPC ........ G08B 21/18; G08B 21/22; G08B 21/24; G08B 21/245; G08B 13/14; G08B 23/00; G06F 19/327; H04N 5/2254
(Continued)

(56) References Cited

U.S. PATENT DOCUMENTS 6,542,568 B1    4/2003   Howes, Jr. et al.
6,707,873 B2    3/2004   Thompson et al.
(Continued)

FOREIGN PATENT DOCUMENTS

WO    WO 2010/141689 A2    12/2010

OTHER PUBLICATIONS

Canadian Office Action dated Feb. 9, 2017 for Application No. CA 2,911,245, 5 pgs.
(Continued)

*Primary Examiner* — Hung T Nguyen
(74) *Attorney, Agent, or Firm* — Frost Brown Todd LLC

(57) ABSTRACT

A system for monitoring and improving hygiene compliance in a caregiver setting is provided. The system includes a plurality of hand cleansing dispensers with sensors coupled thereto to detect usage of the dispenser and the identity of the personnel using the dispenser. Usage of the dispenser affects the personnel's hygiene compliance. Indicators are coupled to or integral with the dispensers to output a real-time indication of the hygiene compliance of the personnel. As time progresses since the last detected handwashing event, the indicators can reflect the real-time degradation of hygiene compliance to keep the personnel well-informed of their compliance.

20 Claims, 8 Drawing Sheets

Related U.S. Application Data

(60) Provisional application No. 61/856,184, filed on Jul. 19, 2013.

(51) Int. Cl.
| | |
|---|---|
| *H04N 5/225* | (2006.01) |
| *H04N 5/369* | (2011.01) |
| *H04N 9/09* | (2006.01) |
| *H04N 5/33* | (2006.01) |
| *A47K 5/12* | (2006.01) |
| *G06F 19/00* | (2018.01) |
| *H01L 27/146* | (2006.01) |
| *A47K 5/14* | (2006.01) |
| *A47K 10/32* | (2006.01) |

(52) U.S. Cl.
CPC ..... *H01L 27/14627* (2013.01); *H04N 5/2254* (2013.01); *H04N 5/33* (2013.01); *H04N 5/3696* (2013.01); *H04N 9/09* (2013.01); *A47K 5/14* (2013.01); *A47K 2010/3266* (2013.01); *H01L 27/146* (2013.01)

(58) Field of Classification Search
USPC ........ 340/573.1, 572.1, 286.07, 286.09, 505, 340/603
See application file for complete search history.

(56) References Cited

U.S. PATENT DOCUMENTS

| | | |
|---|---|---|
| 6,727,818 B1 | 4/2004 | Wildman et al. |
| 7,315,245 B2 | 1/2008 | Lynn et al. |
| 7,477,148 B2 | 1/2009 | Lynn et al. |
| 7,734,476 B2 * | 6/2010 | Wildman .............. G06F 19/327 705/2 |
| 7,755,494 B2 | 7/2010 | Melker et al. |
| 7,898,407 B2 | 3/2011 | Hufton et al. |
| 8,294,584 B2 | 10/2012 | Plost |
| 8,558,701 B2 | 10/2013 | Wegelin et al. |
| 9,131,811 B2 | 9/2015 | Wegelin et al. |
| 9,147,334 B2 | 9/2015 | Long et al. |
| 9,167,941 B2 | 10/2015 | Cittadino et al. |
| 9,188,487 B2 | 11/2015 | Zhevelev et al. |
| 9,226,624 B2 | 1/2016 | Bem et al. |
| 9,497,428 B2 | 11/2016 | Gaisser et al. |
| 2009/0195385 A1 | 8/2009 | Huang et al. |
| 2011/0193703 A1* | 8/2011 | Payton ................. G08B 21/245 340/573.1 |
| 2011/0254682 A1 | 10/2011 | Sigrist Christensen |
| 2013/0094983 A1 | 4/2013 | Pelfrey |
| 2013/0099900 A1 | 4/2013 | Pulvermacher |
| 2013/0120120 A1* | 5/2013 | Long ....................... G06K 7/01 340/10.5 |
| 2013/0122807 A1 | 5/2013 | Tenarvitz et al. |
| 2014/0180713 A1 | 6/2014 | Tenarvitz et al. |

OTHER PUBLICATIONS

Australian Office Action dated Nov. 9, 2016 for Application No. AU 2014290458.
International Search Report and Written Opinion dated Nov. 18, 2014 for Application No. PCT/US2014/047202.
International Preliminary Report on Patentability dated Jan. 28, 2016 for Application No. PCT/US2014/047202.
U.S. Appl. No. 61/557,163, filed Nov. 8, 2011.
U.S. Appl. No. 61/856,184, filed Jan. 19, 2013.

* cited by examiner

| Caregiver: | Smith, Jane RN | | Compliance 55 % |
|---|---|---|---|
| | Room | Time | |
| Compliance | 7918 Pat Rm | 4/12/2010 | 9:16:16AM |
| Noncompliance | 7918 Pat Rm | 4/12/2010 | 9:16:39AM |
| Compliance | 7919 Pat Rm | 4/12/2010 | 9:17:23AM |
| Compliance | 7919 Pat Rm | 4/12/2010 | 9:17:42AM |
| Noncompliance | 7920 Pat Rm | 4/12/2010 | 9:18:19AM |
| Noncompliance | 7920 Pat Rm | 4/12/2010 | 9:19:00AM |
| Compliance | 7918 Pat Rm | 4/12/2010 | 9:27:06AM |
| Noncompliance | 7918 Pat Rm | 4/12/2010 | 9:27:28AM |
| Compliance | 7919 Pat Rm | 4/12/2010 | 9:28:13AM |
| Compliance | 7919 Pat Rm | 4/12/2010 | 9:28:32AM |
| Noncompliance | 7920 Pat Rm | 4/12/2010 | 9:29:10AM |
| Noncompliance | 7920 Pat Rm | 4/12/2010 | 9:29:49AM |
| Compliance | 7918 Pat Rm | 4/12/2010 | 9:37:56AM |

FIG. 7

AUTOMATIC HYGIENE COMPLIANCE ASSISTANCE

CROSS-REFERENCE TO RELATED APPLICATIONS

This application is a continuation of U.S. nonprovisional application Ser. No. 14/335,015 filed Jul. 18, 2014 and issued as U.S. Pat. No. 9,497,428, which claims the benefit of U.S. provisional application Ser. No. 61/856,184 filed Jul. 19, 2013, the disclosures of which is hereby incorporated in its entirety by reference herein.

TECHNICAL FIELD

This present disclosure is directed to hand hygiene compliance, and particularly to assistance to be provided to users in the performance of good hygiene compliance. This disclosure specifically provides for an apparatus which may include dispensary components for dispensing soap and other liquids, and a system for generating signals and producing a visual/audio alerts to assist hygiene compliance.

BACKGROUND

Good hygiene practices, such as hand-antisepsis and wearing of protective garments, are necessary to maintain safety, and it is useful to have an automatic system that will assist persons to perform such personal hygiene tasks. Healthcare associated infections (HAI) lead to greater than a billion dollars in excess healthcare costs annually, which is occurring within an economic environment that is charged with improving patient safety and quality while reducing healthcare costs. Further, pursuant to Deficit Reduction Act (DRA) of 2005 § 5001 (c), the Secretary of Health & Human Services to identify, and reduce payments for, conditions that are: (a) high cost or high volume or both, (b) result in the assignment of a case to a DRG that has a higher payment when present as a secondary diagnosis, and (c) could reasonably have been prevented through the application of evidence-based guidelines. HAIs, thus, exert both a human and economic toll.

Despite recognition of the problem and prior implementation of various hygiene education and disinfection programs, HAI rates remain unacceptably high. Moreover, HAI creates a dilemma for health-care management, because of the worldwide problem of evolving, multi-drug resistant bacteria and the increasing complexity of the healthcare environment. However, the prevailing view is that many HAIs are preventable complications, a view highlighted by the Centers for Medicaid and Medicare Services (CMS) decision that preventable complications, such as vascular-catheter-associated infections, will no longer be reimbursed by Medicare. Other infections may follow.

The etiology of HAIs in health-care settings is explained at least in part by bacterial cross contamination, which is generally believed to be a consequence of poor compliance with best hand hygiene practices. Multimodal intervention strategies have been shown to be more effective than single intervention approaches, but more effective ways must be found to implement such strategies.

It is well known that disease and infection is often transferred from one person to another as a consequence of poor hand hygiene practices by one or more persons in a chain of transmission. The issue is most pronounced in the healthcare industry, including hospitals, care homes and hospices, where visitors and caregivers, including nurses, doctors and therapists, should cleanse their hands regularly. This is especially critical when the persons are moving between treating different patients. Indeed, even patients should be encouraged to be hygienic whenever they exit their room. But the problem is not limited to healthcare institutions. Possibilities for transmitting germs from one person to another are also significant in the hospitality industry where employees have contact with food, service ware, bedding and the public. Schools, day care centers and offices have similar issues. Other environments may also require regular hand hygiene. The environments where good hygienic practices are desirable and should be encouraged are generically referred here as "institutions," and the term includes healthcare facilities such as hospitals, care homes and hospices; facilities involving food handling, such as agricultural facilities, food-processing facilities, catering facilities and restaurants; hospitality facilities, such as hotels and motels; and childcare facilities such as day care centers and schools. All persons within an institution are users of the facility and should be encouraged to maintain good hygienic practices, and, thus, the term "users" is intended to cover all persons within an institution, whether they are employees, third-party contractors, visitors, patients, students or have other reasons for being within an institution.

Healthcare-associated infections (HAIs) are defined as infections not present and without evidence of incubation at the time of admission to a healthcare setting. Within hours after admission, a patient's flora begins to acquire characteristics of the surrounding bacterial pool. It is estimated that in the U.S. alone, there are over 2,000,000 HAIs each year. They conservatively cost $17 billion dollars to resolve and result in 100,000 deaths per year, and nearly one third of these are attributable to poor hand hygiene. Thus, HAIs extract a very high price from society in terms of human pain and suffering as well as treatment and legal costs. Surveillance, along with sound infection control programs, not only lead to decreased healthcare associated infections but also better prioritization of resources and efforts to improving medical care, and programs in health-care institutions to control healthcare-associated infections have been in place since the 1950s. Nevertheless, it is believed that a far more significant portion of these HAIs can be prevented if health care providers practice proper hand hygiene. Indeed, the Centers for Disease Control recognizes that improved hand hygiene compliance with standards for infection control practice is a key to substantially reducing healthcare-associated infections.

Infectious microbes that can be acquired or transmitted in a healthcare setting include: *Acinetobacter baumannii, Burldiolderia cepacia*, chickenpox (varicella), C DIET (*Clostridium difficile*), *Clostridium sordellii*, Creutzfeldt-Jakob Disease (CJD), ebola virus (viral Hemorrhagic Fever), hepatitis viruses A and B, influenzaviruses, MRSA (methicillin-resistant *Staphylococcus aureus*), mumps, norovirus, streptococcal species, *Pseudomonas Aeruginosa*, parvovirus, poliovirus, pneumonia, rubella, SARS, *S. pneumonia*, tuberculosis, VISA (vancomycin intermediate *Staphylococcus aureus*), and VRE (vancomycin-resistant enterococci). MRSA is a type of staph bacteria that is resistant to certain antibiotics called beta-lactams. These antibiotics include methicillin and other more common antibiotics such as oxacillin, penicillin, and amoxicillin. The more severe or potentially life-threatening MRSA infections occur most frequently among patients in healthcare settings. Reducing MRSA in healthcare and other institutions had become a high priority, and recent data indicates that MRSA can be controlled to at least some extent by proper hygienic policies. In 2010, a CDC study showed that invasive (life-threatening) MRSA infections in healthcare settings declined 28% from 2005 through 2008. In addition, the study showed a 17% drop in invasive MRSA infections that were diagnosed before hospital admissions (community onset) in people with recent exposures to healthcare settings.

However, practicing proper hygiene is a difficult task. The failure of workers to employ good hand hygiene practices results from a confluence of factors including lack of knowledge of standards, apathy, time pressures, resistance to change, and perceived inconvenient location of hand disinfection dispensing apparatuses for hand hygiene. Proper hygiene requires following strict rules that demand frequent antisepsis. The major challenge faced by caregivers is that the use of these agents in the quantities and the frequencies necessary to adhere to commonly accepted hand hygiene guidelines results in dangerous and painful degradation of the skin on the users' hands. Resistant strains of pathogens such as MRSA and C DIFF particularly now dictate the use of the harsh rubs and soaps. Following their use, caregivers are encouraged to utilize a secondary skin conditioning agent immediately thereafter to protect their skin from damage.

It must be recognized that not only patient sites, but non-patient sites also are proven sources for hand contamination, including computer keyboards, cell phones, and fixed telephones. New systems and methods designed to encourage, effect, monitor and enforce hand sanitation and other hygienic practices are needed to reduce the spread of infectious microbes in institutions. While the healthcare industry is primarily addressed here, the problems and resultant solutions presented are applicable to a range of industries and service organizations.

Effective implementation of dispensers for soaps, sanitizers and other liquids is useful in the implementation of an overall hand-wash compliance system. Many institutions and industries have provided numerous disposable or refillable (reusable) dispensing containers of sanitizer and/or soap to facilitate individuals in their efforts to sanitize and/or wash their hands. And while the availability of such dispensing containers has increased the opportunities for individuals to wash and/or sanitize their hands, there is still a lack of complete compliance with predetermined hand washing hygiene standards. However, to minimize the potential transmission of bacteria and/or viruses by hand washing and sanitization, full compliance with hygiene standards is required, as the failure of individuals to properly clean and/or sanitize their hands can negate the efforts of others who come in contact with such individuals. Dispensers intended for use in hand-wash compliance systems are known. These include:

U.S. Pat. No. 7,315,245 discloses a method and apparatus involving a soap dispenser base where pressure exerted on a soap dispenser in contact with the soap dispenser base activates a timing means coupled with the base which gives information to the soap dispenser user on the correct duration of time to wash their hands. The base may also include a signal means that the soap dispenser has in fact been utilized. Additionally, the soap dispenser base product may also contain marking mechanisms which are designed to be placed on a variety Of different styles of soap dispensers. The marking mechanisms contain an easily identifiable substance which can only be removed by effective hand washing.

U.S. Pat. No. 6,707,873 discloses a device which measures individual employee usage of a liquid product or hand soap dispenser as part of an overall hygiene compliance program. The dispenser consists of a self-contained keypad/display module which is attached to a standard hand soap dispenser. An employee enters a unique personal ID code and then activates the dispenser. The dispenser counts all inputs to the dispenser in order to generate meaningful data for management. Alternatively, the dispenser may only track and report total usage and not account for individual employee usage.

U.S. Pat. No. 6,542,568 discloses a system for rewarding and encouraging compliance with a predetermined personal hygiene standard in a hygiene compliance program. The system comprises a fluid dispenser. The fluid dispenser includes an actuator. A sensor is connected to the actuator. A processor in electrical communication with the sensor. The processor is configured to increment a count when the sensor is actuated, relate the count to the identification code, and compare the count to a predetermined number.

United States Patent Application Publication No. 2013/0099900 discloses an actuation sensor apparatus configured to removably attach to a liquid dispenser, the apparatus comprising (a) an electronic circuit including a dispense sensor and a wireless transmitter and (b) a power supply for the electronic circuit, whereby, when dispenser actuation occurs, an identification code unique to the apparatus is wirelessly transmitted to a receiver. In a preferred embodiment, the dispense sensor is a magnetic sensor and the apparatus further includes an actuator arm having a magnet, and the actuator arm is configured to move with respect to the magnetic sensor during actuation.

United States Patent Application Publication No. 2013/0076514 discloses a hygiene compliance monitor for a dispensing container that dispenses material when a dispensing nozzle is actuated, includes a flexible main section having a receiving aperture through which the dispensing nozzle extends, so as to enable the main section to be removably attached to the dispensing container. Extending from the main section is a secondary section that is terminated by an attachment sleeve that is configured to removably retain the dispensing nozzle therein. A token, such as a magnet, is carried by the attachment sleeve and is detected by a sensor carried by the main section. Thus, when the dispensing nozzle is actuated to dispense material, the sensor detects the presence and non-presence of the token and accordingly updates a count value that is presented on a display that represents the number of actuations of the dispensing nozzle.

United States Patent Application Publication No. 2013/0122807 is directed to a networked system and method for improving hygiene practices which includes an interactive communication system of user devices and an information engine. Wired and wireless data transmission methods are provided. The networked system and method is incorporated by reference where indicated below with respect to communication between several mechanisms in the hygiene-monitoring system.

United States Patent Application Publication No. 2013/0094983 is directed to a refill unit for a foam dispenser including a liquid container and a diaphragm foam pump connected to the liquid container and diaphragm foam pumps. The diaphragm foam pump includes an elastomeric diaphragm having an air piston bore and a bellows. The air piston bore forms at least a portion of an air chamber. A reservoir is located at least partially within the bellows that includes a liquid inlet. The diaphragm foam pump includes a piston that forms a portion of the air chamber wherein the piston bore may be moved relative to the piston. Movement in a first direction causes air in an air chamber to be compressed and draws liquid into the reservoir and further movement in the same direction causes compressed air to flow into the reservoir where it mixes with the liquid and is expelled as a foam.

United States Patent Application Publication No. 2013/0079923 is directed to a sheet product dispenser includes a housing having a front cover, a main controller, a motor, a dispensing mechanism, a maintenance switch, and an auxiliary feed push button. The motor, main controller and dispensing mechanism are configured to dispense a length of sheet product in response to a signal representative of a request for sheet product.

Unfortunately, current dispensers used in hygiene compliance monitoring systems are not sufficiently helpful in promoting good compliance.

The World Health Organization (WHO) launched a Global Patient Safety Challenge in 2005 and introduced the "5 Moments Of Hand Hygiene" in 2009 in an attempt to reduce the burden of health care associated infections. This model of hand hygiene prompts health care workers to clean their hands at five distinct stages of caring for the patient. The five events are:
- before touching a patient,
- before clean/aseptic procedures,
- after body fluid exposure/risk,
- after touching a patient,
- after touching patient surroundings.

It is an object of this disclosure to provide apparatus to further hand-wash compliance.

A further object of this disclosure is to provide a dispensing apparatus which may be adapted to assist persons in meeting hand-wash compliance requirements.

These and other objects of this disclosure will be apparent from the following descriptions and from the drawings.

SUMMARY

According to one embodiment of the present disclosure, a real-time system is provided for monitoring hygiene compliance within a hygiene tracking environment provided by a real-time tracking apparatus. A plurality of dispensers are configured to dispense a hand-cleansing product. A plurality of auto-ID dispenser tags are each associated with and unique to one of the dispensers. A dispenser sensor is configured to sense an activation of one of the dispensers within the hygiene tracking environment. One or more sensory indicators are communicatively and/or physically coupled to at least one of the dispensers and adapted to controllably indicate hygiene compliance of personnel whose hygiene compliance is desired to be tracked. At least one controller is coupled to a respective dispenser sensor and one or more sensory indicators, the at least one controller programmed to activate or alter the one or more sensory indicators based at least upon a hygiene compliance status of the personnel.

The at least one controller may be further programmed to activate or alter the one or more sensory indicators based at least upon the dispenser sensor sensing an activation of the dispenser. The at least one controller may be further programmed to activate or alter the one or more sensory indicators based at least upon a time elapsing since a previous activation of the dispenser.

The one or more sensory indicators may include audio indicators, such as a speaker configured to output sound indicating the personnel of their hygiene status. The one or more sensory indicators may also or alternatively include a tactile indicator such as a vibrating unit that activates to convey hygiene compliance information to the personnel.

The one or more sensory indicators may include one or more visual indicators, such as LEDs or other lights. The at least one controller may be further programmed to progressively alter the one or more visual indicators as time elapses since the previous activation of the dispenser. The one or more visual indicators may include a plurality of lights, wherein the at least one controller is further programmed to reduce the number of lights that are illuminated based on the time elapsing since the previous activation of the dispenser. The one or more visual indicators may include an illuminated display, wherein the at least one controller is further programmed to change a color of the illuminated display based on the time elapsing since the previous activation of the dispenser.

The at least one controller may be mounted to a local device separate from the dispensers, or may be mounted to the dispenser itself.

The one or more sensory indicators may be part of the dispenser itself, or part of a local device physically separate from but communicatively coupled to the dispenser.

In another embodiment of the present disclosure, a hand-cleansing dispenser for use within a hygiene tracking environment is provided. The dispenser includes a transceiver disposed within a housing and configured to transmit an ID of the dispenser to an off-board server. A sensor is configured to sense an activation of the dispenser. One or more indicators are adapted to controllably output a hygiene compliance status of personnel whose hygiene compliance is desired to be tracked. At least one controller is communicatively coupled to the transceiver, the sensor, and the one or more indicators, wherein the at least one controller is programmed to activate or alter the indicators based at least upon a hygiene status of the personnel.

The at least one controller may be programmed to activate or alter the indicators based at least upon the activation of the dispenser by the personnel.

The one or more indicators may comprise one or more visual indicators. The one or more visual indicators may include a plurality of lights, wherein the at least one controller is further programmed to reduce the number of lights that are illuminated based on the time elapsing since the previous activation of the dispenser. The one or more visual indicators may include an illuminated display, wherein the at least one controller is further programmed to change a color of the illuminated display based on the time elapsing since the previous activation of the dispenser.

The one or more visual indicators may include a row or column of LEDs within a guided path on a designated portion of a face of the dispenser. The at least one controller may be programmed to modify light emitting from the row or column of LEDs based at least upon a time elapsing since a previous activation of the dispenser. The at least one controller may be programmed to modify light emitting from the row or column of LEDs to indicate a hygiene-compliance status. The at least one controller may be programmed to modify a color of the row or column of LEDs based at least upon the time elapsing since the previous activation of the dispenser.

The at least one controller may be further programmed to progressively alter the one or more visual indicators as time elapses since the previous activation of the dispenser.

The at least one controller may be further programmed to, in response to a determination that use of a second dispenser is required for hygiene-compliance, disable use of the dispenser. Use of the second dispenser may be enabled or allowed while the other dispenser is disabled. Audio or visual indication may be provided on the disabled dispenser alerting the personnel to use the second dispenser instead to comply with hygiene requirements.

In another embodiment of the present disclosure, a real-time computer implemented method of monitoring hygiene compliance of personnel within a tracking environment provided by a real-time tracking apparatus is provided. Auto-ID personnel tags are associated with personnel in the tracking environment, with each personnel tag being capable of transmitting a wireless signal including ID information unique to its associated personnel tag. Auto-ID dispenser tags are associated with dispensers in the tracking environment, with each dispenser tag being capable of transmitting a signal including ID information unique to its associated dispenser. The dispenser is capable of dispensing a cleaning agent for hand washing. The method includes assigning a status of hygiene-compliant to a person associated with one of the personnel tags based on a first transceiver associated with one of the dispensers sensing activation of that dispenser indicating a desired handwashing event by the person. The method further includes audibly or visually outputting the status of hygiene-compliant on the dispenser. The method further includes receiving a first signal indicative of the person transitioning from the status of hygiene-compliant to a status of hygiene-noncompliant. Based on the first signal, the method altering the audible or visual output on the dispenser based on the first signal.

The method may include providing a visual display in the form of lights in which their brightness, color, and/or amount of lit lights correspond to the hygiene compliance of the person. As the person becomes more hygiene noncompliant by way of, for example, time passing since a previous handwashing or entering a contamination zone, changing of the lights may indicate such progressive or sudden noncompliance.

In another embodiment of the present disclosure, first and second dispensers are provided, with each dispenser configured to dispense different cleansing agents. Each dispenser includes a transceiver disposed within a housing and configured to transmit a unique ID of the dispenser to an off-board server. One or more indicators are adapted to controllably output a hygiene compliance status of personnel whose hygiene compliance is desired to be tracked. One or more controllers is configured to (i) receive a signal indicating that use of the second dispenser is required for hygiene compliance, and (ii) activate or alter the one or more indicators on the first dispenser to direct the personnel to use the second dispenser for hygiene compliance.

Each dispenser may also include a sensor configured to sense an attempted activation of the dispenser.

Each dispenser may include a mechanical lever that, when translated, causes a pump to dispense a cleansing agent.

The signal given to and/or by the at least one controller may vary based on the location of the personnel, the diagnosis of the patient in the vicinity of a local device detecting the personnel, the previous handwashing or hygiene compliance of the personnel, and other conditions. Based on these conditions, the at least one controller may be configured to alter the one or more indicators accordingly.

In one example, the first dispenser is a sanitizer dispenser, and the second dispenser is a soap dispenser. Based on the various conditions, the at least one controller causes the sanitizer dispenser to display a visual indication that soap is required for hygiene compliance. The at least one controller may also temporarily disable the use of the sanitizer dispenser. The disabling of the sanitizer dispenser may last so long as the system determines that the personnel whose hygiene compliance is monitored is attempting to use the sanitizer dispenser.

BRIEF DESCRIPTION OF THE DRAWINGS

FIG. 7 is one example of a hygiene-compliance report for one caregiver utilizing the dispensers according to at least one embodiment of the present disclosure.

DETAILED DESCRIPTION

Figures 1A, 1B:
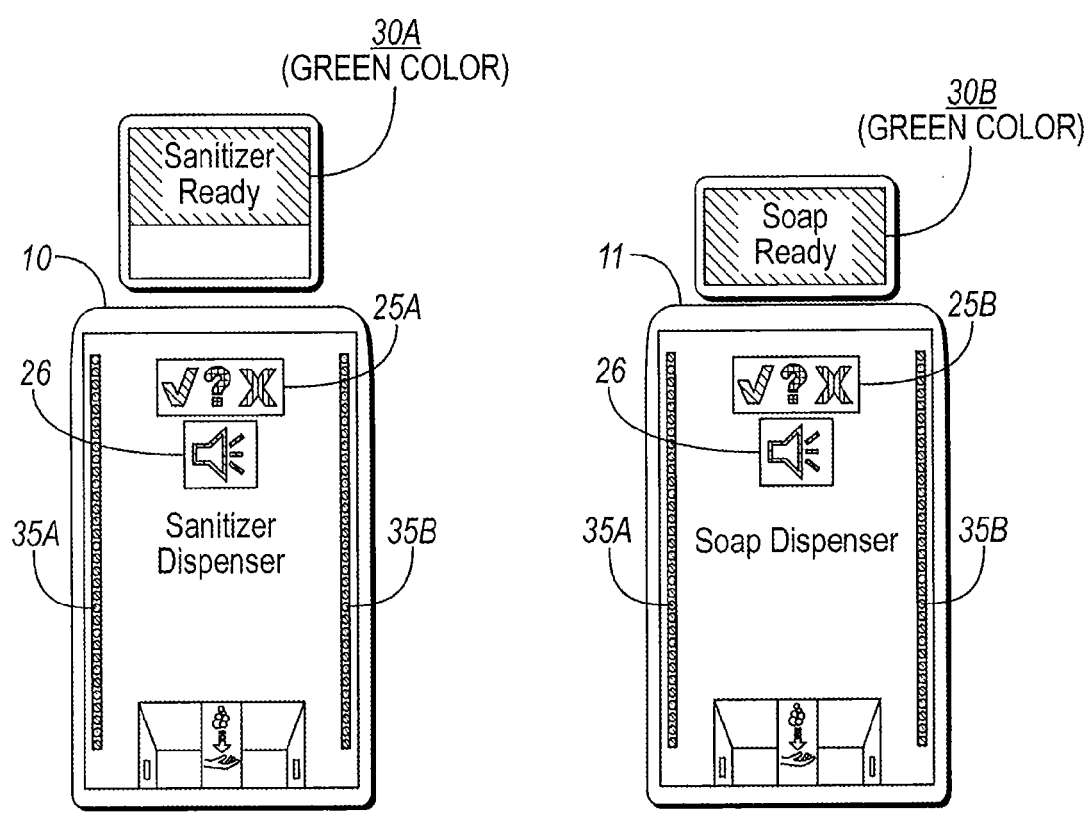
FIG. 1A is a front view of a sanitizer dispenser and FIG. 1B is a front view of a soap dispenser according to one embodiment of the present disclosure.

Embodiments of the present disclosure are described herein. It is to be understood, however, that the disclosed embodiments are merely examples and other embodiments can take various and alternative forms. The figures are not necessarily to scale; some features could be exaggerated or minimized to show details of particular components. Therefore, specific structural and functional details disclosed herein are not to be interpreted as limiting, but merely as a representative basis for teaching one skilled in the art to variously employ the embodiments. As those of ordinary skill in the art will understand, various features illustrated and described with reference to any one of the figures can be combined with features illustrated in one or more other figures to produce embodiments that are not explicitly illustrated or described. The combinations of features illustrated provide representative embodiments for typical applications. Various combinations and modifications of the features consistent with the teachings of this disclosure, however, could be desired for particular applications or implementations.

Dispensers

According to various embodiments, a sanitizer dispenser 10 and a soap dispenser 11 are provided. It should be understood that "sanitizer" and "soap" are mere examples; the dispensers 10 and 11 are capable of dispensing two different cleaning agents, for example. The cleaning agents being dispensed can be a substance used to cleanse a part of a body, such as hands, or an article, such as a medical cart, for hygienic purposes, and particularly for controlling the quantity of infectious agents on the skin of a user or on the object. The cleaning agents can include, but are not limited to, water-based and waterless compositions. The term generally encompasses hand rubs, antimicrobial and/or antiseptic soaps, detergents, soaps, waterless antiseptic agents, and surgical hand scrubs. The cleaning agents may be in the form of a solid (e.g., bar of soap, surgical prep sponge), powder, liquid, cream, spray, gel, or the like. An alcohol-based hand rub is an alcohol-containing preparation designed for application to the hands for reducing the number of viable microorganisms on the hands. An antimicrobial soap refers to a product comprising soap or detergent and an antiseptic agent. A detergent or soap is a product that includes compounds that possess a cleaning action. They are composed of both hydrophilic and lipophilic parts and can be divided into four groups: anionic, cationic, amphoteric, and nonionic detergents. Although products used for hand hygiene or antiseptic hand wash in health-care settings represent various types of detergents, the term "soap" also refers to such detergents. In summary, the dispensers 10, 11 are capable of dispensing two different types of cleaning agents.

The dispensers 10, 11 may also be configured to dispense sheets, such as paper towels and liquid-impregnated sheets, the sheets including natural and/or synthetic woven and/or non-woven cloth and/or paper sheets.

The dispensers 10, 11 are also configured to communicate (either wirelessly or by wire) the operation status and identity of the dispenser, as will be described below. Such structure in the communication system is described in U.S. Patent Publication No. 2013/0122807 (U.S. Ser. No. 13/671,303) to Tenarvitz et al., the description of which is here incorporated by reference. The dispensers are preferably located close to the patient bed in patient rooms, at the entrance of patient rooms, in examination and procedure rooms, in any specialized medical room dedicated for diagnostic and therapeutic procedures, and also in areas such as preparation rooms for baby formula, aseptic areas such as cornea transplant banks, or blood transfusion units, on trolleys used for storage and transport of wound care products, in the anterooms of isolation units and operating theatres, in sanitary rooms of medically used areas, or at the entrance of hospitals and intensive care units.

In a preferred embodiment, the dispenser is activated or triggered without using hands. This can be accomplished by use of elbow-operated actuators, but more preferably the dispensing of liquid is activated or triggered by a sensor that registers the presence of a hand in the area where the dispensing article is to be released. Dispensers must be operated and maintained such that a microbial contamination of the pump nozzle or other dispenser outlet is avoided.

Figure 5:
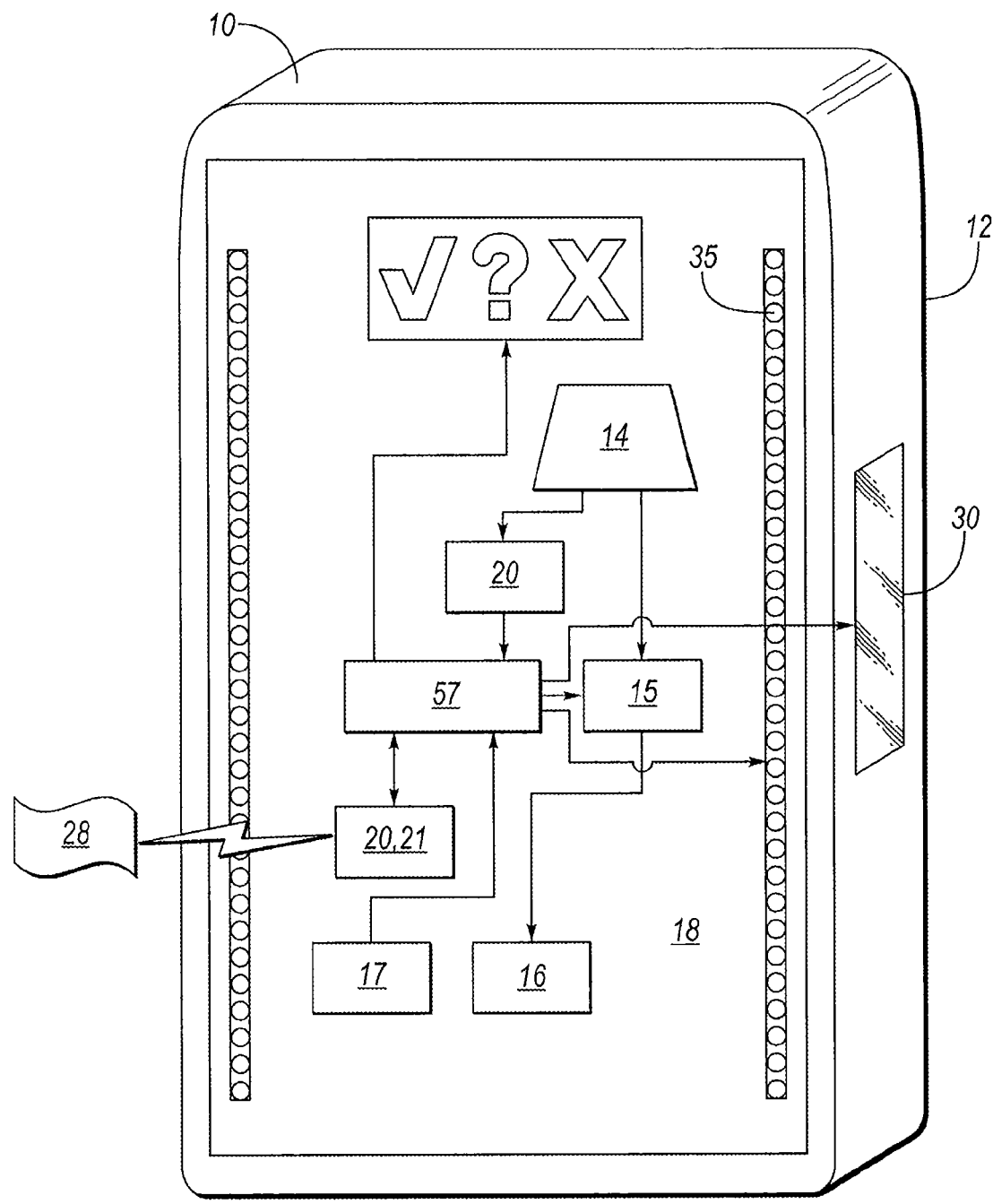
FIG. 5 is a schematic block diagram illustrating a dispenser constructed in accordance with at least one embodiment of the present disclosure.

The dispenser 10, 11 comprises a housing 12 that generally includes sides separated by front and back surfaces. The dispenser also includes an outlet port 16 positioned generally at a lower portion of the housing, but may also be locate intermediate top and bottom, and may be a pump at the top or above the dispenser. The outlet port is in communication with a cleaning agent source. An actuator may be provided that dispenses the cleaning agent in response to a sensor sensing a proximity of an object (e.g., hand) indicating an intended use of the dispenser, as will be further described below. The dispenser 10, 11 preferably includes a cavity 18 for removably receiving a sealed replaceable reservoir or cartridge 14. Refillable containers have been reported to be subject to contamination, and, therefore, the hand-wash compliance cleaning agents are preferably contained in a sealed replaceable reservoir or cartridge, so that the dispenser can be refilled without risk of contaminating the liquid. The contours of the walls of cavity are designed to accommodate one or more geometries for the replaceable reservoir or cartridge. As shown in FIG. 5, sensor 17 is included in the cavity for communicating a signal to microcontroller 57 when the replaceable reservoir or cartridge is positioned within cavity, or to identify and signal the state of filling of the replaceable reservoir or cartridge. An inexpensive alternative to the sensor 17 may be a spring loaded switch 20 communicating a signal to microcontroller 57 that the refills weight has been reduced to the point that it can no longer overcome the switch reset spring. The microcontroller 57 may disable pump 15 if sensor 17 or spring loaded switch 20 indicate that material requires replenishment. The disperser can be specific to a proprietary replaceable container or allow different types of containers from different suppliers to be utilized.

The dispenser preferably has a downward sloping top to prevent items from being placed atop it. The dispenser preferably allows easy cleaning and disinfection of the exterior and interior of the dispenser.

The housing can be molded from an elastomeric material. Particularly where patient security may be a consideration, the dispenser can also be made from steel, such as 14 and 16-gauge stainless steel, and be made without any easily removable external parts or sharp edges that patients can break and use to hurt staff members, other residents, or themselves. The dispenser should not protrude more than four inches from the vertical surface it is mounted on to ensure compliance with the Americans with Disabilities Act. Dispensers can include locks, such as circular key-way cam-lock, to prevent patients and others from opening the dispenser to drink or contaminate the cleaning agents.

Most preferably, the dispenser is designed with materials that can be subjected to both chemical and thermal disinfection. It should be possible for the dispenser to operate consistently and accurately dispense the desired quantity of liquid, powder, sheet or other material for hundreds of actuations without failure. The dispenser enclosure may include receptors for IR signals or other communication mode, and may include regions for increased transmission of communication of ultrasound or other communication modes for which the enclosure may constitute a barrier.

The combination of container and dispenser should not allow any physical degradation of the hand-wash compliance agent inside the container, or reduction of the concentration of the one or more active ingredients in the container.

The dispenser for liquids or powders includes a pump 15 for pumping liquid or flowable powder from the container and into and through an outlet port 16 having a dispensing opening for dispensing the material. The pump may include a component for creating foam or otherwise injecting another material to combine with the liquid. Pumps that are usable in the present disclosure for dispensing liquids are disclosed in, for example, U.S. Patent Publication No. 2013/0094983 (U.S. Ser. No. 12/272,443).

A sheet dispenser typically utilizes rolls of sheet product, which are dispensed from the roll by passing one end of the sheet product through a pair of rollers. With electrically operated dispensers, one of the rollers is coupled to an electric motor that is selectively energized by a microcontroller 57 or other microprocessor or controller. Friction between the rollers and the sheet product pulls the sheet product from the sheet product roll when the motor is operated. Some type of separation arrangement, such as perforations with or without a tear-bar, is also provided for allowing a portion of the sheet product roll to be removed from the dispenser by a user.

Dispensing systems for sheets are disclosed in U.S. Patent Publication No. 2013/0079923 (U.S. Ser. No. 13/240,645).

The dispenser should allow visual indication to make it possible to easily identify the liquid, powder or sheet material in the dispenser and the quantity of material remaining in the replaceable container without any manipulation of the dispenser. An embodiment is disclosed below.

Component of Hand-Wash Compliance System

The dispenser is preferably part of a more comprehensive hand-wash compliance system and a comprehensive real-time location system (RTLS), as described in U.S. Patent Publication No. 2013/0122807 to Tenarvitz et al., the description of which is here incorporated by reference. The following describes a preferred embodiment or implementation of the present disclosure as part of an RLTS system, and the term "preferably" is included in every description that follows.

The RLTS system will include both a personal device, such as a tag 112 (FIG. 8) worn by users or attached to objects, and a local device. The personal device can be an electronic device, such as a tag, carried with a user or attached to an object within the tracking environment providing communications between that user and systems operating in the environment. The local device comprises one or more dispenser components, which are able to electronically assist users in the proper utilization and consumption of the hand-wash compliance liquids, to control the amounts of hand-wash compliance agents being used, the length of time being used, give indications to the user, and communicate information to the information engine. The local device can refer to an electronic device stationed within a given area of an environment providing communication between any user within the given area of an environment and systems operating within that environment.

Dispensers 10, 11 or other local device(s) will incorporate microcontroller 57. The microcontroller 57 will typically be located within the dispenser housing or housing of another local device, but may also be attached to the exterior or be otherwise in communication with the dispenser. The functionality of the microcontroller 57 may be distributed among multiple units that each provides more limited functionality to discrete portions of the operation of the local device. The main microcontroller 57 can be a microprocessor located in a remote location. For example, the control functions can be provided by a hygiene monitoring system wherein the microcontroller 57 logic is provided by a main processor coupled to an information engine as therein described. In such case, the dispenser will still require a slave or auxiliary microcontroller 57 to activate and otherwise control the dispenser functions.

Microcontroller 57 includes a processor (CPU) and memory. The CPU may provide processing capability to execute an operating system, run various applications, and/or provide processing for one or more of the techniques described here. Applications that may run on the microcontroller 57 may include, for example, software for managing and performing content, software for using the resources of other chips or electronic devices. Microcontroller 57 is preferably programmable. The programing may be provided by wireless or wired communications from the information engine to the receiver 20, which then communicates the information to the memory component of the microcontroller. The microcontroller may similarly direct the transmitter 21 to communicate information by wireless or wired communications from the local device to the information engine.

The CPU may represent one or more microprocessors, and the microprocessors may be a combination of special-purpose microprocessors or application-specific integrated circuit, or ASIC.

Dispensers 10, 11 or other local device(s) will also incorporate a receiver 20. Receivers 20 of the local device, whether a dispenser or other apparatus, may incorporate a transmit function and thereby be transceivers, or the transmit function may be by a separate transmitter component 21. In any event, the dispenser or local device will normally include both receive and transmit functions. Both receivers 20 and transmitters 21 will be part of, or in communication with, microcontroller 57 and can generally be referred to as a transceiver.

The CPU or processor, memory, receiver 20 and transmitter 21 may be single integrated multi-tasking system-on-a-chip that constitutes all or part of the microcontroller 57, or the processor, memory, receiver 20 and transmitter 21 may be a series of chips or other components in communication with each other or in communication with a central point. The memory may also be a separate component, or a cache of the processor, including one or more of flash, SRAM, ROM and EEPROM.

The microcontroller 57 may be programed to respond to the identification of the user entering into the room as reflected by the personal device worn by the user. The RTLS personal devices identify which user has entered into a contamination zone or other area, which permits the local device to respond with advice, cues, alerts or instructions, and to store information relating to the hygienic status of the user, such as whether the user has actuated one or more of the dispensers 10, 11. Alternatively, the local device can transmit the information relating to the user and the user's activities to the information engine 28, and thereafter may receive a response from the information engine indicating the instructive functions which the local device can then execute. The information engine 28 may include the one or more processors similar to microcontroller 57. The information engine is aware of the location of the dispensers, and thus, data transmitted back to the network, if properly encoded with the identity of the dispenser, includes the identity of the user actuating dispensers in a known location.

As noted previously, generally, microcontroller 57 provides logic and control functionality used during operation of the dispenser. The microcontroller 57 will, for example, receive a signal from a sensor indicating a hand washing event is desired, determine the amount liquid or powder to be dispensed, and control the amount of sheet product dispensed. One means of controlling the amount of dispensed material is by timing the operation of the motor coupled to the pump or to the rollers. In another embodiment, the dispenser includes a quantity sensor indicator. In such an embodiment, the indicator may be used for verifying that the amount of cleaning agent which is released in a personal hygiene event, such as hand antisepsis, is sufficient for increasing the hygiene level of the user. Optionally, the quantity sensor includes a scale for measuring the weight of the hygienic agent in the dispenser. Optionally, the indicator includes a camera or other optical sensor for estimating a change in the amount of the cleaning agent. It should be noted that any sensor which may be used for detecting an amount change may be used as a quantity sensor. In such a manner, the indication of a dispensing of a sufficient amount of cleaning agent is considered as a personal hygiene event and is communicated to the information engine. On the other hand, a change, which is indicative of an insufficient amount of cleaning agent, is considered as a failure to perform a personal hygiene event.

Microcontroller 57 is preferably networked by an interface, such as Ethernet, or wireless protocols such as IEEE 802.11a/b/g/n or Wi-Fi, and specifically receiver 20 and transmitter 21 can be designed to communicate by wireless means or any wired means, and may include advanced communication capabilities, including one or more of 10/100 Ethernet MAC/PHY and CAN controllers, and may include a serial interface. A main memory may be communicably coupled to the CPU, which may store data and executable code. The main memory may represent volatile memory such as RAM, but may also include nonvolatile memory, such as read-only memory (ROM) Or Flash memory. In buffering or caching data related to operations of the CPU, the main memory may store data associated with applications running on the electronic device. The microcontroller 57 may also include nonvolatile storage. The nonvolatile storage may represent any suitable nonvolatile storage medium, such as a hard disk drive or nonvolatile memory, such as Flash memory. Being well-suited to long-term storage, the nonvolatile storage may store data files, software (e.g., for implementing functions on the microcontroller 57), monitoring information (e.g., information obtained from the dispenser), transaction information (e.g., information such as use of the soap dispenser), wireless connection information (e.g., information that may enable the device to establish a wired or wireless connection), and security information. It should be appreciated that data associated with sharing resources with certain other electronic devices, such as resource-sharing software plug-ins, may be saved in the nonvolatile storage.

Among other functions, microcontroller 57 is configured and programmed to respond to the dispense sensor 17 by transmitting a signal including a unique identification code associated with dispenser via the wireless or wired transmitter of each particular embodiment.

The pump or roller motor is disposed within the housing in operable communication with the microcontroller 57. The dispensing mechanism is disposed within the housing in operable communication with the motor, wherein the microcontroller 57, the motor and the dispensing mechanism are configured to dispense an amount of material in response to a signal representative of a request for the material. The microcontroller 57 is responsive to executable instructions to facilitate actuation of the motor and the dispensing mechanism in response to a signal from the microcontroller 57 or from a manual input, such as the user pressing on a button. Alternately or additionally, the dispenser may include an auxiliary mechanism, such a manual feed lever or button, for manually operating the pump or rollers to provide material without the need for a microcontroller 57 or any electric power.

Actuation of the dispenser is typically on-demand, when a microcontroller 57 receives a signal that a user requests or "demands" material, such as users presenting their hands near a proximity sensor. The proximity sensor signals the microcontroller 57 to initiate a new dispense cycle. A sheet dispenser can alternately operate via a "Hang-Mode," where the dispenser automatically presents for the taking a user-portion of sheet product upon the tearing away of prior sheet. Thus, upon removal of the user-portion by a user, a tear sensor is activated that initiates a new dispense cycle. The "Hang Mode" is less preferred, because the sheet is more exposed to the environment.

Surveillance sensors or hygiene event sensors are disposed for detecting users' utilization of the hygienic station. The proximity sensors are local devices. The sensing system, such as reflective optical detection system, such as an infrared sensor, senses a user's hand beneath the dispensing opening of the spout for activating the pump for pumping the liquid, or in close proximity to the sheet discharge to dispense rolling sheets. With infrared sensors, if a user's hand is beneath the spout or in close proximity to the dispensing chute, the pulse is generated by a source and is reflected back by the user's hand to a photo detector. If the microcontroller 57 determines that an object is beneath the spout, the pump is activated to discharge a predetermined amount of the liquid. When the dispenser is actuated, a motorized pump or other dispensing unit dispenses the liquid from the refill cartridge through the spout or other outlet port. The system may also include a light to simultaneously illuminate the spout Or other outlet port area.

In the same fashion as above, a sheet roller will be activated when persons' hands are indicated to be in close proximity to the discharge chute.

The sensing system may, alternately, utilize Near-Field Communication as described in U.S. Patent Publication No. 2013/0122807 (U.S. Ser. No. 13/671,303) to Tenarvitz et al.

The sensing system should reduce power consumption to the minimum, so that the dispensers can be powered by batteries.

Physical Presence Detector

The dispenser or local device may include a physical presence detector or sensor which may be incorporated within the devices or be provided, as a separate component that is in wired or wireless communication with microcontroller 57. The physical presence detector or sensor will indicate that a human Or an object has entered into a designated area, even if the person or object does not include a personal device. Microcontroller 57 can then base its hand-wash compliance assistance functions in response to that signal from the detector/sensor. The detector/sensor may be powered by any suitable source, such as but not limited to a power source derived from the input voltage to the dispenser, or from other sources such as a battery, solar power source, mechanical or thermal power source, etc., or any combination of these, etc. The detector/sensor may be activated by motion, sound, thermal, voice or other indicia of physical presence, or any combination of the above. These can be, in particular, passive detectors that sense body heat, those that send out pulses of ultrasonic waves and measure the reflection off a moving object, microwave active sensor that send out microwave pulses and measures the changes due to reflection off a moving object similar to a police radar gun, and tomographic systems that sense disturbances to radio waves. Many existing detectors use dual-technologies, but these have to be well configured to decrease the frequency of "false positives," while increasing the detectors' efficiencies.

The detector/sensor may be in a form that will distinguish between, for example, a casual appearance in the doorway and entry into a room. Timers may be included to allow the microcontroller to terminate control and reporting functions after the physical presence is no longer detected.

In one embodiment, upon sensing the entry of a person into a designated area, such as a hospital room, the detector sends a signal to the microcontroller which communicates with the information engine. If the recognition of the entry of the person into the area does not coincide with the entry of a personal device into the same area, the system assumes that a person is not a person who is an employee or a patient, and will assume that hand-wash compliance instructions are necessary. The information engine therefore will instruct the system to provide audio or visual instructions to the person to commence the prescribed hand-wash sequence, using the same cues as otherwise here set forth. If the person does not follow the required sequence, an alert may be sent to the appropriate recipient.

Assistance with Hand-Wash Compliance

The local device's recognition system, whether receiver 20 or a physical presence detector or sensor, will communicate information that a person or object has entered a defined zone. That information will be communicated in the first instance to microcontroller 57, and may be further communicated to information engine 28. In either case, the microcontroller 57 may assist users in the performing the necessary proper hand hygiene utilizing the cleaning agent, protective agent and/or drying agent.

In one implementation, the dispensers 10, 11 of the hand-wash compliance system includes receiver 20, which will receive a signal from a personal device, such as a tag of user, that the user has entered into a hospital room or other designated area. The microcontroller may be sufficiently programmed to recognize the user and respond at least in part to the user's entry without further communication with the information engine. In other words, the microcontroller is the information engine. In another implementation, microcontroller causes the transmitter 21 to communicate to a remote information engine that a defined user has entered into the designated area, which engine will process the information, and reply to the microcontroller with the instructions or other information to perform certain actions in response to the entry.

Thereafter, based upon embedded instructions or instructions communicated from the information engine, the microcontroller will direct the subsequent steps in response to the user's entry, and the actions or activities of the user within the area, including the performance of the hand-wash compliance program established for the institution, the designated area and the user. The quality of the events which are detected by the hygiene event sensors may be based on a cumulative value that is calculated by combining data from some or all of a plurality of hygiene event sensors. For example, a sum, a mean, and/or an average of the qualities which has been given to a certain hygiene event by a plurality of hygiene event sensors may be used for determining the quality of an event In one embodiment, the information engine logs the identified hygiene events. Each hygiene event is preferably tagged with a time stamp that reflects the time, or the approximate time, in which the relevant hygiene event has been identified. The time stamp may be based on the clock of the processor and/or on an external clock, such as a real time clock. In another embodiment, the microcontroller 57 logs the identified hygiene events in memory of the microcontroller 57, which may later be communicated to the information engine 28.

In use, the location detecting module may log information about the location of the user, optionally with association to a respective time stamp, which is optionally taken from the information engine. For example, FIG. 7 depicts an exemplary dataset of logged personal hygiene events. Each personal hygiene event is time and location tagged. Optionally, the quality of the personal hygiene event is documented when available.

The dispenser may be remotely managed utilizing standard protocols, or, alternatively, the station may incorporate an interface for communicating with the microcontroller 57, whether located within the dispenser or remote.

The microcontroller 57 can communicate information relating to the utilization of the dispensers. For example, the microcontroller can cause the transmitter 21 to communicate to the information engine 28 whether a set time passed between the dispensing of the cleaning agent and the release of the protective agent and/or the drying agent, to confirm that scrub time was maintained for the particular environment. The information engine 28 may also be configured to enter a content query mode, and send a remote content query to the local device. Upon receiving the query, the local device performs an inventory check and reports the results to the information engine.

Assistance to Users

As shown in FIGS. 1-4, the dispenser may include a mechanism to provide one or more visual indicators 25A, 25B so as to inform an observer of the status of the dispenser such as a green check indicating normal dispenser function, a yellow question mark indicating service likely required soon (for example, the supply of material or that battery power is running low is low) and a red "X" indicating the dispenser has failed and requires service (for example, the supply of material or battery power is exhausted). As also shown in FIGS. 1-4, the dispenser may include a mechanism to provide one or more acoustic indicators 26 so as to inform an observer via unique tones of actions required to remain complaint with a particular process. One form of the indicator comprises one or more light-emitting-diodes (LEDs) that indicate whether the device is properly functioning, or alternatively that, for example, the supply of material is running low or is exhausted, or that battery power is low.

In addition, as shown in FIGS. 1-4, the dispenser further comprises a second indicator 35A, 35B to provide caregivers or other users with visual indication of their hygiene compliance. The second indicator is preferably a light source, such as an LED or array of LEDs. In one particularly preferred embodiment, the optical indicator signaling the user is in the form of a light path along at least one side of the enclosure, and preferably around the side and top perimeters of the dispenser housing. The light path comprises or is coupled to light sources that can wholly or partially illuminate the light path with different colors. The light path may comprise a longitudinal light conducting member or tube, which is end lighted by a least one light source. Alternatively, the longitudinal light conducting member is shaped as a light conducting core member, wherein electrical conductors rim parallel with the light conducting core member in a light conducting cladding. The light emitting means may also comprise distinct light emitting objects arranged along the path. Thus, separate LEDs may be provided along the path to be lighted in accordance with a prescribed algorithm. The light may also be pulsating, flashing or change color in order to improve visibility, to signal to the user that the user is to utilize a certain dispenser, or to use for a specified length of time, as part of the handwash compliance program.

In one embodiment the second indicators 35A, 35B may emit red, yellow and green colors, and are produced by LED lights in the interior of the light path around the perimeter of the dispenser. In one embodiment, the light source comprises at least one first light-emitting diode (LED) situated inside the inner volume of the light source mounted to the first end part of the light path, and at least one second light-emitting diode situated inside the inner volume of the light source and mounted to the opposite or second end part of the light path. Each of the at least one first and at least one second light-emitting diode emits light along a main beam path, wherein the main beam path is oriented along the direction of the tube. In particular, the at least one first LED and the at least one second LED emit light in opposite directions, i.e., the at least one first LED emits light directed toward the second end part, whereas the at least one second LED emits light toward the first end part. The interior of the light path includes a flexible foil or other reflecting sheet formed the desired shape and can cover arbitrarily formed interior surfaces of the tube, and at the two ends of the light path. The light path is preferably air-filled, to ease manufacturing and avoid need to fill with special gases as for example inert gases.

The lights are in communication with the microcontroller 57, which may be in communication with at least one remote information engine 28, or the microcontroller may be programed to act without further communication with a remote information engine.

The dispenser also comprises a housing 12 that may include a window aperture 30 (30A, 30B) in which text or an image can be disposed. The aperture provides information useful in enforcing handwash compliance systems and validating proper compliance has occurred. The window aperture 30 may be a personal device carried by the user or on a local device stationed in the same area as the dispenser.

Figure 2A:
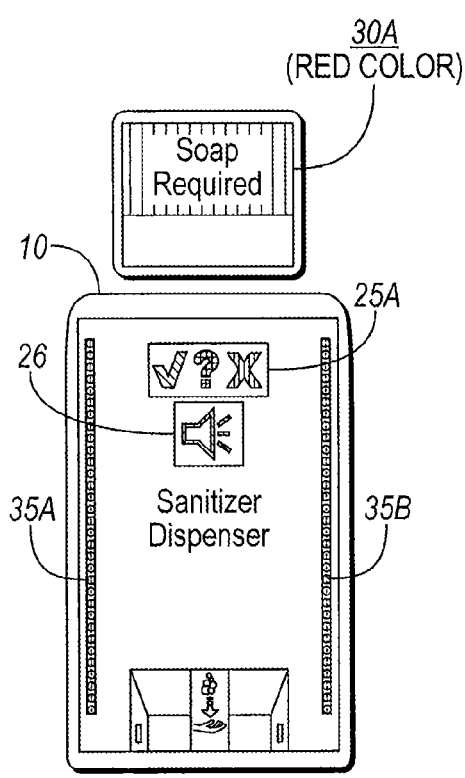
FIGS. 2A and 2B are front views of the sanitizer dispenser and soap dispenser of FIGS. 1A and 1B, respectively, illustrating one embodiment of a visual indication or alert provided by the sanitizer dispenser.
Figure 2B:
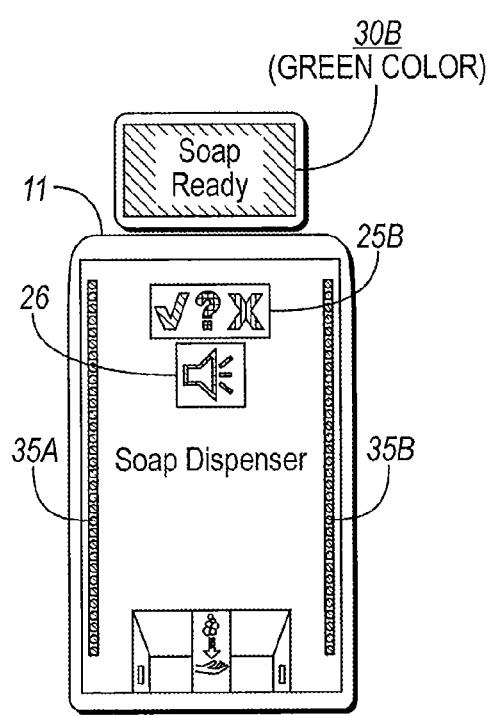

The light paths 35A, 35B may be substituted by the window aperture 30, or the two may be used jointly. The window aperture 30 may be integral to the dispenser, a personal device carried by the user or a local device stationed in the same area as the dispenser. Under certain conditions the information engine may decide that conditions demand a soap and water wash is required for hygiene compliance. As shown in FIG. 2A, light path 35A of the dispenser may turn a red color indicating to the user that sanitizer cannot or should not be used for hygiene compliance, the microprocessor 57 may disable the pump 15 in dispenser 10 containing sanitizer, window aperture 30A may instruct the user that "Soap Is Required" and the acoustic indicator 26B may sound a unique tone associated with "Soap Required". The users place their hands under dispenser 11 containing soap, at which point the microcontroller 57 directs the pump to deliver a pre-determined amount of liquid from the outlet port of dispenser 11. Thereafter, the system may direct the users to perform other elements of the hand-wash compliance regime, such as invoking protective aids. The visual, audible, and/or tactile notifications described elsewhere in the present disclosure can also be commanded by the microprocessor to notify a user that another dispenser is required for hygiene compliance.

As described above, when conditions require use of one dispenser 11 versus another dispenser 10 for proper hygiene compliance, the controller may disable the use of the dispenser 10 and/or provide an alert that use of the other dispenser 11 is required. Such disabling can be made via a mechanical device that actuates to inhibit a path in which a lever or handle travels in order to dispense the cleansing product from the pump 15. For example, a controller may activate an actuator that moves a blocking device to prevent the lever of the dispenser from full movement, thereby preventing the cleaning agent from being dispensed. Alternatively, if the cleansing agent can be dispensed automatically due to a signal received by a proximity sensor, the controller can cause the signal that is normally sent from the sensor to be blocked. This example and other examples are contemplated that can cause the disabling of the dispenser when activation of the dispenser would not result in proper hygiene compliance.

The conditions that may require use of one dispenser versus another for proper hygiene compliance include knowledge of the diagnosis of the patient within a room in which the dispensers are housed, time elapsed since a previous handwashing event, or a previous locations of the personnel (e.g., within a contamination zone). Of course, these conditions are merely exemplary and other conditions are contemplated that would require use of one dispenser (e.g., sanitizer) instead of another (e.g., soap).

Figure 3A:
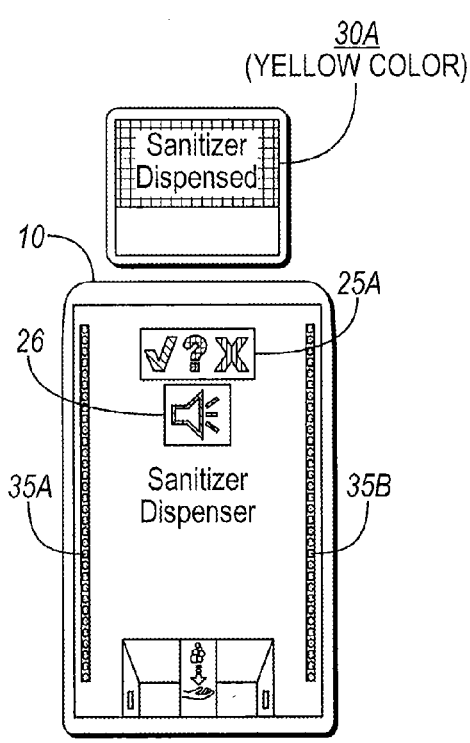
FIGS. 3A and 3B are front views of the sanitizer dispenser and soap dispenser of FIGS. 1A and 1B, respectively, illustrating one embodiment of a visual indication or alert provided by both the sanitizer dispenser and the soap dispenser.
Figure 3B:
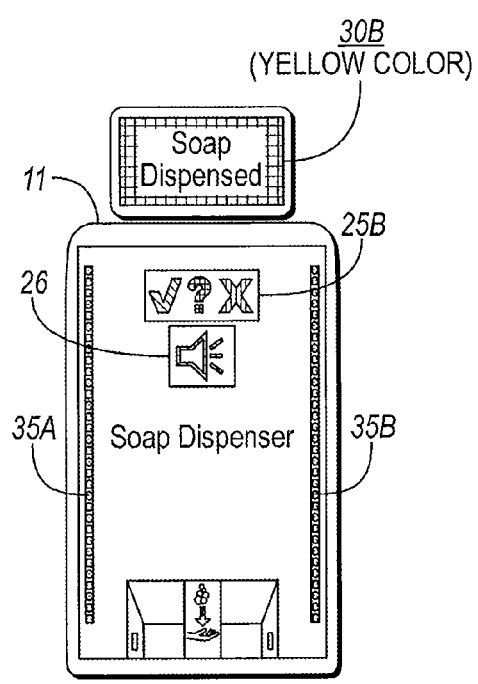

As shown in FIGS. 3A, 3B, the dispenser may acknowledge dispensing the required cleaning agent and feedback may be provided to the user if additional required steps must be completed.

In short, in response to either the hygiene-status of the personnel, or in response to the attempted use of the dispenser 10 when such use would not solve an unacceptable hygiene-compliance status, the microprocessor may disable the pump and/or provide a visual indication that use of the other dispenser 11 is required for hygiene compliance.

Figure 4A:
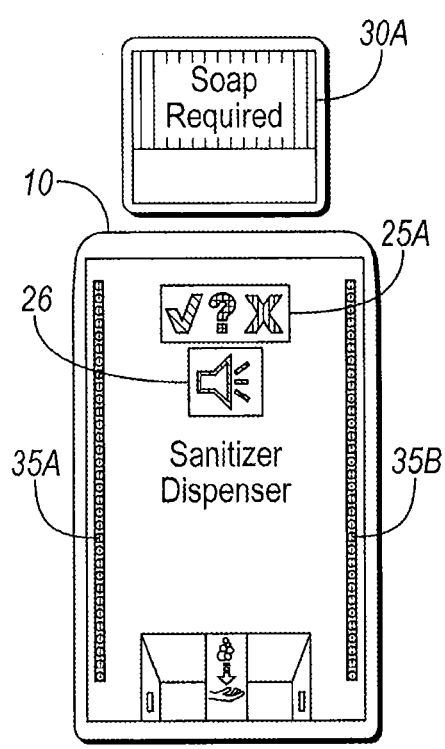
FIGS. 4A and 4B are front views of the sanitizer dispenser and soap dispenser of FIGS. 1A and 1B, respectively, illustrating other embodiments of visual indications or alerts provided by the sanitizer dispenser and the soap dispenser.
Figure 4B:
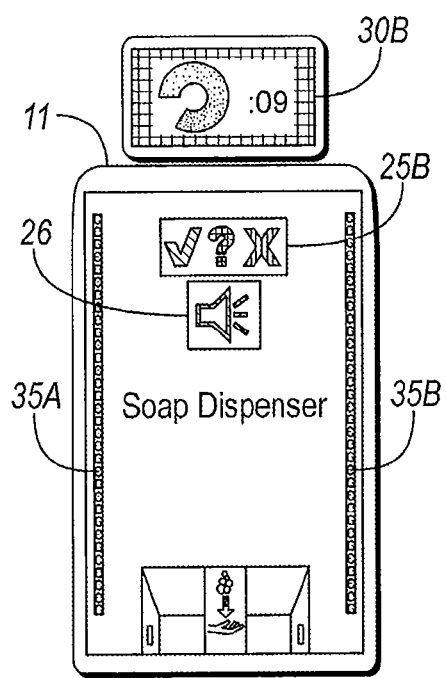

As shown in FIG. 4B, indicators may be designed to help users monitor their progression through the healthcare provider's handwashing protocol. Window aperture 30B illustrates a countdown timer that may help users wash their hands for the requisite period of time, which may be a universal time or a time specific to a given contamination zone or other indicia. In addition an acoustic indicator 26B may sound a unique tone, and or the visual indicator 35B may light a specific color indicating that the necessary time period has elapsed. The information engine 28 may be programmed to trigger indicators 26A-B, 30A-B and 35A-B in either a random or a predetermined escalation sequence to compensate for users attention that may have been compromised by alarm fatigue or other common distractions.

In short, a pre-programmed timer function may be enabled based on use of the dispensing unit by a personnel, indicating the time remaining for proper hand washing. Additionally, expiration of the timer (which may vary for different areas/zones or for different patients) subsequent to the hand cleansing event can indicate that the personnel is no longer hygiene-compliant. While the timer is counting down, the light sources 35A, 35B may also change in number of illuminated lights, overall intensity, and/or color (see, e.g., FIGS. 6A thru 6C and associated description below).

It is recommended by the Centers for Disease Control and Prevention that hands should be rubbed together with soap for 10 to 15 seconds for the hands to be cleaned thoroughly. However, many users rush and are not cognizant of the actual length of time devoted to cleaning, and thus usually fail to thoroughly clean their hands, thus creating opportunities for germs to spread. The present timer may function in response to this need. When users position their hands below the dispenser, the sensor signals the microcontroller to activate the pump or rollers. At the same time, the microcontroller initiates the timer in order to activate the indicators 30, 35. The dispenser includes, in particular, light path 35 and aperture 30, which can be used as visual timers during the performance of hand-wash compliance actions. In other words, the timer may count down the amount of time left for the length of hand washing. Such a timer is shown in FIG. 4B and is generally designated with reference numerals 30 and 35. The microcontroller 57 includes a memory wherein cleaning constants are stored, which dictate the boundary conditions of the target cleaning process.

In particular, a standard cleaning time and a minimum cleaning time for an effectual cleaning process can be stored in the memory.

The controller signals one or both of light path 35 and aperture 30 to indicate the time necessary to wash hands and/or to countdown the cleaning time required by the hand-wash compliance protocol. The timer may continue its countdown so long as local device 20 continues to receive indication that the user is in proximity to the hand-wash hygiene station. Upon timer termination, indication is given for successful completion of the protocol. On the other hand, if the proximity sensor determines that the user has not remained in proximity to the hygiene station for the full amount of time, the visual indicators 30 and/or 35 can emit different warning signals, which indicate deviations to the user. The deviation can also be recorded or noticed to other systems. The deviation can additionally be enhanced by voice instructions from speakers associated the hygiene monitoring system. Thereafter, the system may direct the users to perform other elements of the hand-wash compliance regime, such as invoking protective aids or directing microcontroller 57 or other microprocessor to energize an electric motor coupled to the rollers to dispense towels.

The information engine may conduct a compliance check to compare the results of the users' hand-wash compliance actions against the information stored in a database. If the reported results of the hygiene station match the database requirements, the user is deemed to be compliant. However, if the results do not match the requirements set forth in the database, then the user is deemed to be non-compliant. In the event that a user is non-compliant, the information engine may include a rule to communicate the user's state to hospital staff or other personnel by triggering an indicator such as flashing red lights of light path 35.

Thus, the information engine, whether wholly or partly remote or wholly or partly part of the microcontroller, may prescribe a hygiene regime for a given patient or hospital room. When a user enters a contamination zone or other designated area, a transceiver associated with the user's personal device communicates the user's presence to the information engine, or a detector or sensor recognizes the entry of a person without a personal device. The information engine, directly or indirectly, determines the hand-wash compliance regime appropriate for the particular user and the particular environment. At the time of entry into the contamination zone, the dispensers are in their normal protocol state, as shown in FIG. 1A, 1B, which means that the dispensers act as passive documentation devices, collecting and communicating information regarding dispenser usage and interaction, and providing assistance to the user.

Scenario Examples

The functioning of the present disclosure may be illustrated by the following examples. The examples include illustrative functionality that will the address the "5 Moments Of Hand Hygiene" and specifically provide assistance with hand-wash procedures:

before touching a patient,
before clean/aseptic procedures,
after body fluid exposure/risk,
after touching a patient,
after touching patient surroundings.

Solution 1—Assisting individuals with compliance through a visual signal communicating exactly when to perform hand hygiene.

When a user enters a designated area such as a hospital room, the local device recognizes the user as one who does not have a record of having performed a hand-wash compliance regime within the frame programmed by the institution. The light path around the soap dispenser, therefore, lights up in color red, indicating to the user to begin a hand-wash compliance procedure. The color indicator is particularly helpful to the caregiver in a crisis situation. The lighted colors remind the caregiver of the procedure to be followed, and inform the patient that the patient must wait the completion of hand-wash compliance before the caregiver can attend the patient. The processes, methods, or algorithms disclosed herein can be deliverable to/implemented by a processing device, controller, or computer, which can include any existing programmable electronic control unit or dedicated electronic control unit. Similarly, the processes, methods, or algorithms can be stored as data and instructions executable by a controller or computer in many forms including, but not limited to, information permanently stored on non-writable storage media such as ROM devices and information alterably stored on writeable storage media such as floppy disks, magnetic tapes, CDs, RAM devices, and other magnetic and optical media. The processes, methods, or algorithms can also be implemented in a software executable object. Alternatively, the processes, methods, or algorithms can be embodied in whole or in part using suitable hardware components, such as Application Specific Integrated Circuits (ASICs), Field-Programmable Gate Arrays (FPGAs), state machines, controllers or other hardware components or devices, or a combination of hardware, software and firmware components.

Alternately, or in addition, the information engine may have a record that the caregiver or other user had performed hand-wash compliance sometime in the past. Looking now at FIG. 6, generalized hand-wash compliance percentage performance thresholds, each with associated colors, tones and other attributes, may be preset for any given clinical area. An example of these may be:

1. GREEN: 100%-67%, Acceptable (FIG. 6(C))
2. YELLOW: 66%-34%, Marginal (FIG. 6(B))
3. RED: 33%-0%, Unacceptable (FIG. 6(A))

Figure 6A:
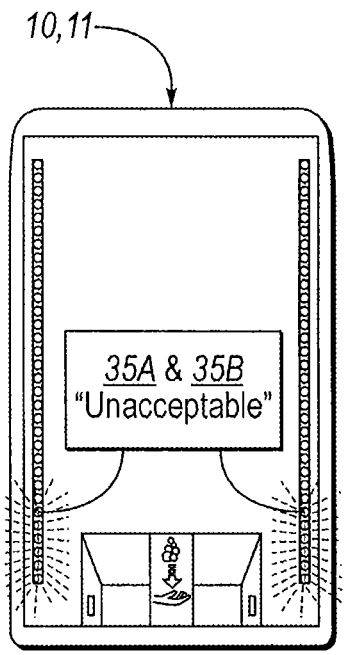
FIGS. 6A, 6B and 6C are front views of a sanitizer dispenser, illustrating a change in lighting corresponding with hygiene compliance according to at least one embodiment of the present disclosure.
Figure 6B:
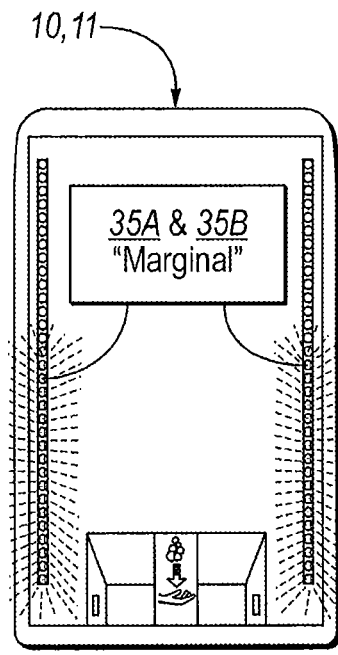
Figure 6C:
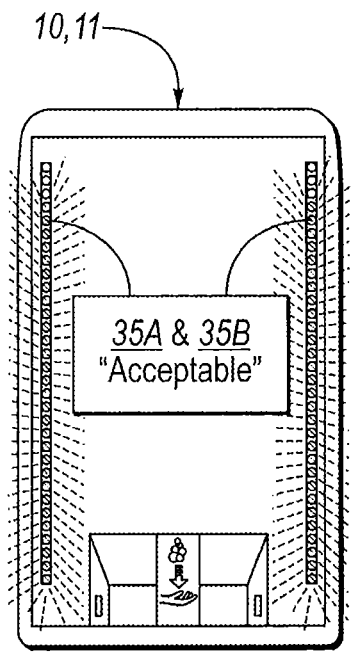

When the user's entry into the contamination zone is registered, microcontroller 57 may illuminate the second indicator 35A, 35B based upon the user's hand-wash compliance from the most recent recorded period. As shown in FIGS. 6A-6C, microcontroller 57 may light a section of the total indicator 35A, 35B proportional to the user's hand-wash compliance in a color that was preassigned to the category the user fall into. As time elapses since a previous hygiene-compliant status of the user, the lighted section of the total indicators may progressively decrease, and the color may also change (e.g., from green to yellow to red).

When the user's entry into the contamination zone is registered, microcontroller 57 may invoke an "exception protocol," and indicate required activity to the user by a series of visual indications. An "exception" protocol can be initiated to require users to utilize certain sanitizing methods when conditions warrant (such as during infection control protocols) before entering and or leaving the contaminated zone. This exception protocol can be controlled centrally, or automated with a rules engine (based on information from the patient record, room assignment information in the nurse call or bed management system etc.) Feedback to the user when dispenser is used is provided automatically through optional devices, such as invoking the red color lighting of light path 35A, and/or providing directions window aperture 30.

Thus, the light path may change in the length of to the light path is illuminated, or have a change in color, which advises the caregivers or users of the length of time allowed in a patient zone before they need to perform hand hygiene. Thus, the users place their hands under the soap dispenser, after which the protective agent dispenser lights up indicating that the user is to apply the protective agent. After the protective agent dispenser is activated, all the lights may be terminated or be turned to a color (for example, green) indicating that hand-wash compliance has been satisfied.

Solution 2—Lighting displays individual's participation score through light color and length indicating low, average, or above average percentage to provide supportive feedback in the moment, encouraging compliance through competition and visual reminders.

Caregiver A and caregiver B enter a designated area. Caregiver A performs hand-wash compliance. Caregiver B goes directly to the patient bedside. Via communication between the tags worn by the caregivers and the local device, the microcontroller had recognized that two persons have entered with only one having complied with the hand-wash compliance procedures. The light path turns red, and potentially pulsates at a safe frequency. Caregiver B asks caregiver A why the lights are red and flashing, and caregiver A instructs caregiver A on the steps to be followed for hand-wash compliance.

Solution 3—Light signal displays when a soap and water wash is required based on patient diagnosis at the moment, without compromising privacy or dignity.

Patient C in the hospital room has contracted *C. diff*. Caregiver A and caregiver B are in the designated area assisting Patient C. Caregiver A receives a pager or mobile phone message to go to another area. The caregivers prepare to leave and Caregiver A grabs a sanitizing wipe and cleans the phone quickly. Both caregivers use the alcohol rub dispenser to clean their hands, heading toward the door. But, the light path around the soap dispenser remains red and is brightened or pulsating. Caregivers now recall that the room was *C. diff* contaminated, that a soap and water cleaning was required after caring for this type of patient. The caregivers wash their hands as required, and once the microprocessor recognizes the soap being dispensed for the individual caregivers, the light paths extinguishes and the small green light in the lower right-hand corner provides compliance positive feedback. Alternatively, or in addition, the panel of LEDs may change from red to green, and may be fully lit to 100% compliance.

Solution 4—Lighting that Decreases in Length Communicating Timing.

WHO's fifth key hand-wash compliance moment occurs after contact with patient surroundings. In other words, when the devices within the dispenser recognize and sense the caregiver as entering within an area of the patient, compliance status may shift to "non-compliant," and the dispensers may reflect an unacceptable hygiene-compliance status according to any of the strategies described above. The light path may be programed to remind caregivers inside a designated area to refresh their hand-wash compliance procedures at programed time frames.

Thus, the present disclosure does not merely remind caregivers, family visitors or other users to comply with hand-wash compliance procedures, but assists such persons by directing the persons to the appropriate dispenser, instructing them on the length of time required to perform the each step, and any other protocol that may be required.

It is of course contemplated that the exemplary scenarios above can be accomplished on other local devices rather than (or in combination with) the dispensers themselves. For example, lights and/or audio indications can be mounted on signal receivers (local devices) stationed within the patient care room that are not part of the dispenser. These local devices can then change color and/or sound based on the hygiene compliance of the personnel. Along with or alternative to audio and visual indicators, tactile indications (e.g., vibration) can be utilized to indicate the hygiene compliance of the personnel. For example, the personnel tag can include a vibrator mechanism coupled to the microprocessor M the tag such that the vibrator mechanism activates when a transition from hygiene-compliance to hygiene-noncompliance is occurring. In a particular example, the tactile indicator may activate based on the hygiene-compliance transitioning from 34% compliance to 33% compliant (i.e., the scenario in which the LED lights alter from yellow to red in Solution 1 above). In short, for all embodiments and solutions disclosed in the present disclosure, the visual, audio, and/or tactile indicators ("sensory indicators") can be provided on any local device or tag in the environment and are not necessarily only provided a dispenser.

Communication System

Figure 8:
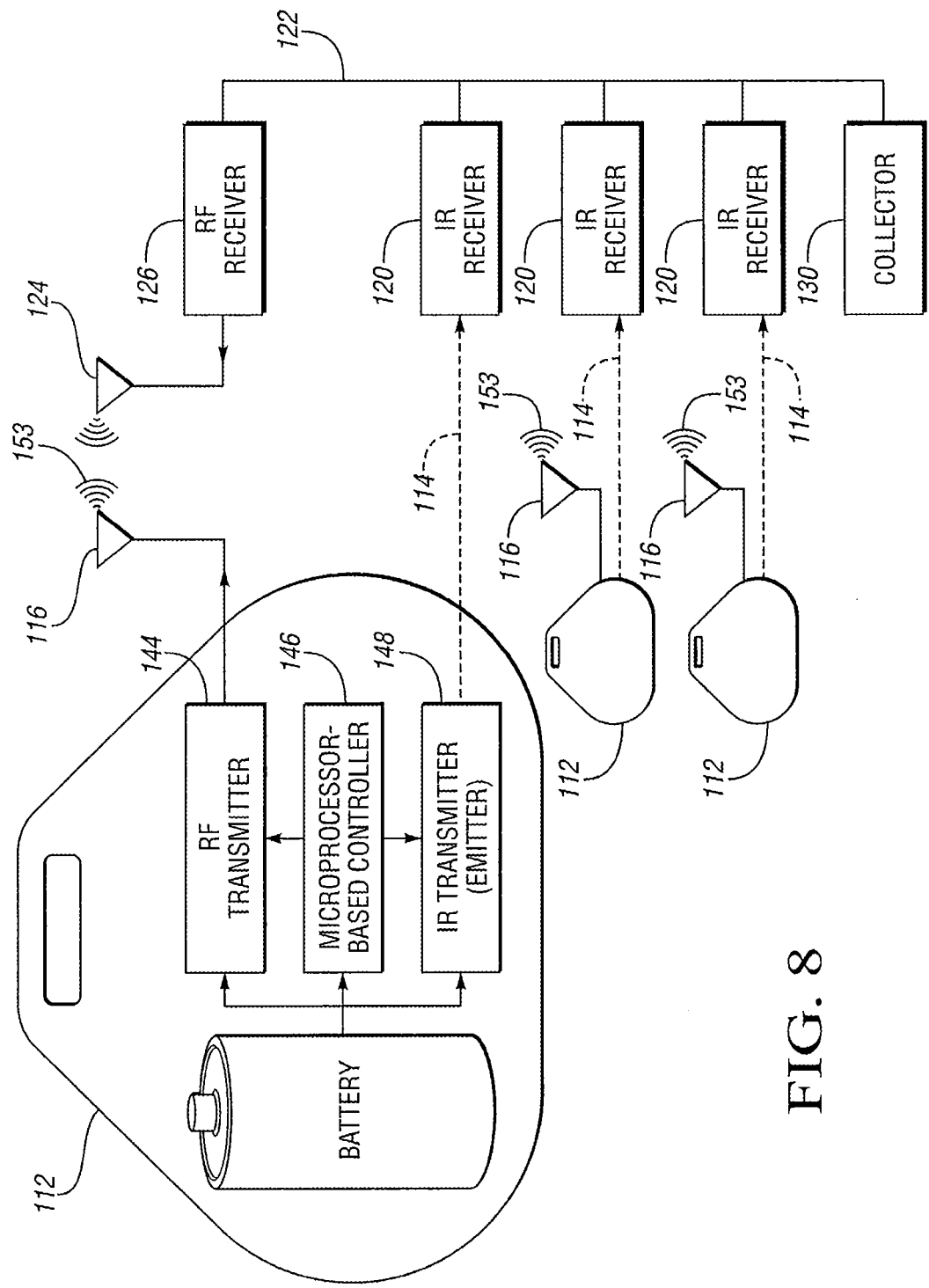
FIG. 8 is a schematic block diagram specifically illustrating an auto-ID tag for sending identification information of personnel within a tracking environment.

FIG. 8 is a schematic of a system for providing communication of data between the various components described above. The system comprises tags 112 (worn by personnel or users, or attached to the dispensers themselves, or attached to another local device) which emit infrared (i.e. IR) signals 114 which are captured by infrared receivers 120 common to the tracking system (e.g., within the dispensers, on the walls, in the patient's rooms, etc.). Upon activation of dispenser 10, 11, a transceiver in the dispenser 10, 11 reads an IR signal 114 from a caregiver badge, adds a data element which identifies the caregiver badge to its own identifying data element, and transmits a qualified badge signal which includes the two identifying data elements via an IR emitter or RF transmitter. This enables an off-board server to receive and store information indicative of the identity of the personnel and the dispenser being used. The off-board server then can, via a controller, command a local microcontroller to activate or alter the sensory indicators according to the previously-described embodiments.

The maximum effective line-of-sight range of such infrared signals 114 may be about a twenty meter diameter with the transceiver. To achieve higher granularity within the system, the infrared receiver 120 may have its field of view reduced to as little as a one meter diameter by introducing a restrictor in the IR sensor. The tags 112 may also transmit radio frequency (i.e., RF) signals 153 which are received by an RF receiver 126. The radio frequency signal 153 emitted by the antennas 116 are received by an antenna 124 of a radio frequency receiver 126. Typically, information is collected using an in-ceiling and/or in-wall serial network that terminates at the microprocessor-based collector 130. The collected information may be sent from either one or both of the user's tag 112 and the transceiver or tag within the dispenser 10, 11.

If the IR receiver 120 is not within the dispenser and rather stationed within the wall or other structure, it is stationary with its location known. The dispenser 10, 11 may or may not be stationary. Tags 112 are worn by mobile subjects and transmit unique IDs 114 which allow the tracking system to associate unique subject identifiers (such as physician, nurse or patient) to each individual tag 112. With this association, when IR signals 114 are received by an IR receiver 120 or dispenser transceiver, and the tracking system identifies the tag(s) 112 (and hence the subject or subjects) relative to the location of the IR receiver. The tracking system aggregates the unique IDs received from the tags 112 enabling the system to identify when one or more unique IDs are present at a particular location (represented by an IR sensor 120). The tracking system also calculates the amount of time that has passed since last receipt of each IR signal 114 at an IR sensor 120 or specialized transceiver.

Since it is important that certain tag-wearing subjects identified as givers of care (i.e., caregivers) to patients perform a hand cleansing event prior to interacting with other tag-wearing subjects identified as patients, the tracking system recognizes when a subject with a caregiver tag 112 activates the dispenser 10, 11 to deliver hand cleaning agent. To accomplish this, an IR receiver 120 of the transceiver or tag within or proximate the dispenser scans the area directly in front of the dispenser 10, 11 when it is activated to detect an IR transmission 114 from the tag 112. The microprocessor-based controller (e.g., 57) adds a data element which identifies the caregiver tag to its own identifying data element and transmits a modified badge signal including the two identifying data elements via an IR emitter or RF transmitter. Alternatively, identifying signals may be sent separately.

While exemplary embodiments are described above, it is not intended that these embodiments describe all possible forms encompassed by the claims. The words used in the specification are words of description rather than limitation, and it is understood that various changes can be made without departing from the spirit and scope of the disclosure. As previously described, the features of various embodiments can be combined to form further embodiments of the present disclosure that may not be explicitly described or illustrated. While various embodiments could have been described as providing advantages or being preferred over other embodiments or prior art implementations with respect to one or more desired characteristics, those of ordinary skill in the art recognize that one or more features or characteristics can be compromised to achieve desired overall system attributes, which depend on the specific application and implementation. These attributes can include, but are not limited to cost, strength, durability, life cycle cost, marketability, appearance, packaging, size, serviceability, weight, manufacturability, ease of assembly, etc. As such, embodiments described as less desirable than other embodiments or prior art implementations with respect to one or more characteristics are not outside the scope of the disclosure and can be desirable for particular applications.

What is claimed is:

1. A method of monitoring hygiene compliance within a hygiene tracking environment, the method comprising:
(a) associating at least one indicator with a dispenser disposed within the hygiene tracking environment, wherein the dispenser is configured to facilitate hand-cleansing;
(b) sensing a physical presence of a person proximate the dispenser;
(c) in response to sensing the physical presence of the person proximate the dispenser, determining a hygiene compliance status associated with the person, wherein the hygiene compliance status indicates hygiene compliance or hygiene non-compliance;
(d) indicating the hygiene compliance status via the at least one indicator;
(e) sensing activation of the dispenser by the person;
(f) in response to sensing activation of the dispenser by the person, updating the hygiene compliance status associated with the person; and
(g) indicating the updated hygiene compliance status via the at least one indicator.

2. The method of claim 1, further comprising:
updating the at least one indicator based at least in part on a time elapsed since a previous activation of the dispenser.

3. The method of claim 1, further comprising:
changing a visual characteristic of the at least one indicator progressively based at least in part on a time elapsed since a previous activation of the dispenser.

4. The method of claim 1, further comprising:
(a) associating a personnel tag with the person; and
(b) sensing the personnel tag to sense the physical presence of the person proximate the dispenser.

5. The method of claim 1, further comprising:
(a) associating a dispenser tag with the dispenser;
(b) sensing the dispenser tag to determine the dispenser is within the hygiene tracking environment.

6. A method of monitoring hygiene compliance within a hygiene tracking environment, the method comprising:
(a) associating at least one indicator with a dispenser disposed within the hygiene tracking environment, wherein the dispenser is configured to facilitate hand-cleansing;
(b) sensing a physical presence of a person proximate the dispenser;
(c) determining whether the person is associated with a personnel tag;
(d) in response to determining the person is not associated with a personnel tag, providing instructions to the person to commence a hygiene compliance sequence via the at least one indicator;
(e) in response to determining the person is associated with a personnel tag, collecting a hygiene compliance status associated with the person, wherein the hygiene compliance status indicates hygiene compliance or hygiene non-compliance; and
(f) in response to the hygiene compliance status indicating hygiene non-compliance:
providing instructions to the person to commence the hygiene compliance sequence via the at least one indicator;
(ii) sensing activation of the dispenser by the person; and
(iii) in response to sensing activation of the dispenser by the person, updating the hygiene compliance status associated with the person to indicate hygiene compliance.

7. The method of claim 6, further comprising:
in response to the hygiene compliance status indicating hygiene non-compliance, indicating hygiene non-compliance via the at least one indicator.

8. The method of claim 7, further comprising:
in response to updating the hygiene compliance status associated with the person to indicate hygiene compliance, indicating the updated hygiene compliance status via the at least one indicator.

9. The method of claim 7, further comprising:
updating the at least one indicator based at least in part on a time elapsed since a previous activation of the dispenser.

10. The method of claim 7, further comprising:
changing a visual characteristic of the at least one indicator progressively based at least in part on a time elapsed since a previous activation of the dispenser.

11. The method claim 6, further comprising:
in response to sensing activation of the dispenser by the person, displaying a timer via the at least one indicator.

12. A system for monitoring hygiene compliance of a person desired to be tracked within a hygiene tracking environment, the system comprising:
(a) a dispenser configured to dispense a hand-cleansing product;
(b) a dispenser sensor configured to sense an activation of the dispenser and send a signal of the activation to affect a hygiene compliance status of the person;
(c) an indicator at the dispenser configured to controllably indicate hygiene compliance and non-compliance of the person; and
(d) a controller communicatively coupled to the dispenser sensor and the indicator and programmed to actuate the indicator based at least upon the hygiene compliance status of the person.

13. The system of claim 12, wherein the controller is programmed to actuate the indicator based at least upon the dispenser sensor sensing an activation of the dispenser.

14. The system of claim 12, wherein the controller is programmed to actuate the indicator based at least upon a time elapsing since a previous activation of the dispenser.

15. The system of claim 12, wherein the indicator includes a visual indicator.

16. The system of claim 15, where the controller is programmed to progressively alter the visual indicator as time elapses since the previous activation of the dispenser.

17. The system of claim 15, wherein the visual indicator includes a plurality of lights, wherein the controller is programmed to reduce the number of lights that are illuminated based on the time elapsing since the previous activation of the dispenser.

18. The system of claim 15, wherein the visual indicator includes an illuminated display, wherein the controller is programmed to change a color of the illuminated display based on the time elapsing since the previous activation of the dispenser.

19. The system of claim 12, wherein the controller is mounted to a local device system separate from the dispenser.

20. The system of claim 12, wherein the controller is mounted to an off-board control system separate from the dispenser.

* * * * *